(12) United States Patent
Rowe et al.

(10) Patent No.: US 8,469,925 B2
(45) Date of Patent: Jun. 25, 2013

(54) BALLOON CATHETER INCLUDING MULTIPLE CHAMBER BALLOON WITH VARYING RADIUS

(75) Inventors: Todd Rowe, Excelsior, MN (US); David Broman, Rogers, MN (US); Benjamin Gundale, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 392 days.

(21) Appl. No.: 12/820,345

(22) Filed: Jun. 22, 2010

(65) Prior Publication Data

US 2010/0262076 A1 Oct. 14, 2010

Related U.S. Application Data

(63) Continuation of application No. 11/367,778, filed on Mar. 3, 2006, now Pat. No. 7,740,609.

(51) Int. Cl.
*A61M 31/00* (2006.01)
*A61M 37/00* (2006.01)
*A61M 29/00* (2006.01)

(52) U.S. Cl.
USPC ............ 604/103.07; 604/101.01; 604/103.05; 604/103.06

(58) Field of Classification Search
USPC ............... 604/96.01, 101.01–101.05, 103.01, 604/103.03–103.07, 103.11–103.14; 606/192, 606/194
See application file for complete search history.

(56) References Cited

U.S. PATENT DOCUMENTS

| | | | |
|---|---|---|---|
| 4,338,942 A | 7/1982 | Fogarty | |
| 4,546,759 A | 10/1985 | Solar | |
| 4,581,017 A | 4/1986 | Sahota | |
| 4,744,366 A | 5/1988 | Jang | |
| 4,958,634 A | 9/1990 | Jang | |
| 4,994,033 A | 2/1991 | Shockey et al. | |
| 5,002,532 A | 3/1991 | Gaiser et al. | |
| 5,019,042 A | 5/1991 | Sahota | |
| 5,074,845 A | 12/1991 | Miraki et al. | |
| 5,158,540 A | 10/1992 | Wijay et al. | |
| 5,273,536 A | 12/1993 | Savas | |
| 5,304,135 A | 4/1994 | Shonk | |
| 5,308,323 A | 5/1994 | Sogawa et al. | |
| 5,308,356 A * | 5/1994 | Blackshear et al. | .......... 606/194 |
| 5,415,635 A | 5/1995 | Bagaoisan et al. | |
| 5,423,745 A | 6/1995 | Todd et al. | |
| 5,462,529 A | 10/1995 | Simpson et al. | |
| 5,484,412 A | 1/1996 | Pierpont | |
| 5,536,252 A | 7/1996 | Imran et al. | |
| 5,658,311 A | 8/1997 | Baden | |
| 5,807,331 A | 9/1998 | Den Heijer et al. | |

(Continued)

FOREIGN PATENT DOCUMENTS

DE 10010467 9/2001
DE 20110989 9/2001

*Primary Examiner* — Laura Bouchelle
*Assistant Examiner* — Nathan R Price
(74) *Attorney, Agent, or Firm* — Vidas, Arrett & Steinkraus, P.A.

(57) ABSTRACT

A catheter assembly may comprise a guide catheter, a balloon catheter with a steering balloon and a stabilizing balloon and a guide wire. The stabilizing balloon secures the balloon catheter to the guide catheter while the steering balloon secures the catheter assembly to the vessel wall. In another embodiment, the balloon catheter has three balloons engaged to the exterior surface, a steering balloon, a stabilizing balloon and an anchoring balloon.

10 Claims, 6 Drawing Sheets

U.S. PATENT DOCUMENTS

| | | |
|---|---|---|
| 5,833,650 A | 11/1998 | Imran |
| 5,865,801 A | 2/1999 | Houser |
| 5,947,924 A | 9/1999 | Liprie |
| 6,267,747 B1 | 7/2001 | Samson et al. |
| 6,485,500 B1 | 11/2002 | Kokish et al. |
| 6,524,302 B2 | 2/2003 | Kelley |
| 6,544,222 B1 | 4/2003 | Yang |
| 6,616,629 B1 | 9/2003 | Verin et al. |
| 6,632,196 B1 | 10/2003 | Houser |
| 6,776,771 B2 | 8/2004 | van Moorlegem et al. |
| 6,966,889 B2 | 11/2005 | Saab |
| 2002/0010418 A1 | 1/2002 | Lary et al. |
| 2002/0026145 A1 | 2/2002 | Bagaoisan et al. |
| 2002/0032406 A1 | 3/2002 | Kusleika |
| 2003/0028211 A1 | 2/2003 | Crocker et al. |
| 2003/0050600 A1 | 3/2003 | Ressemann et al. |
| 2004/0054347 A1 | 3/2004 | Zadno-Azizi et al. |
| 2004/0092870 A1 | 5/2004 | Squire et al. |
| 2004/0147811 A1 | 7/2004 | Diederich et al. |
| 2005/0075662 A1 | 4/2005 | Pederson et al. |

* cited by examiner

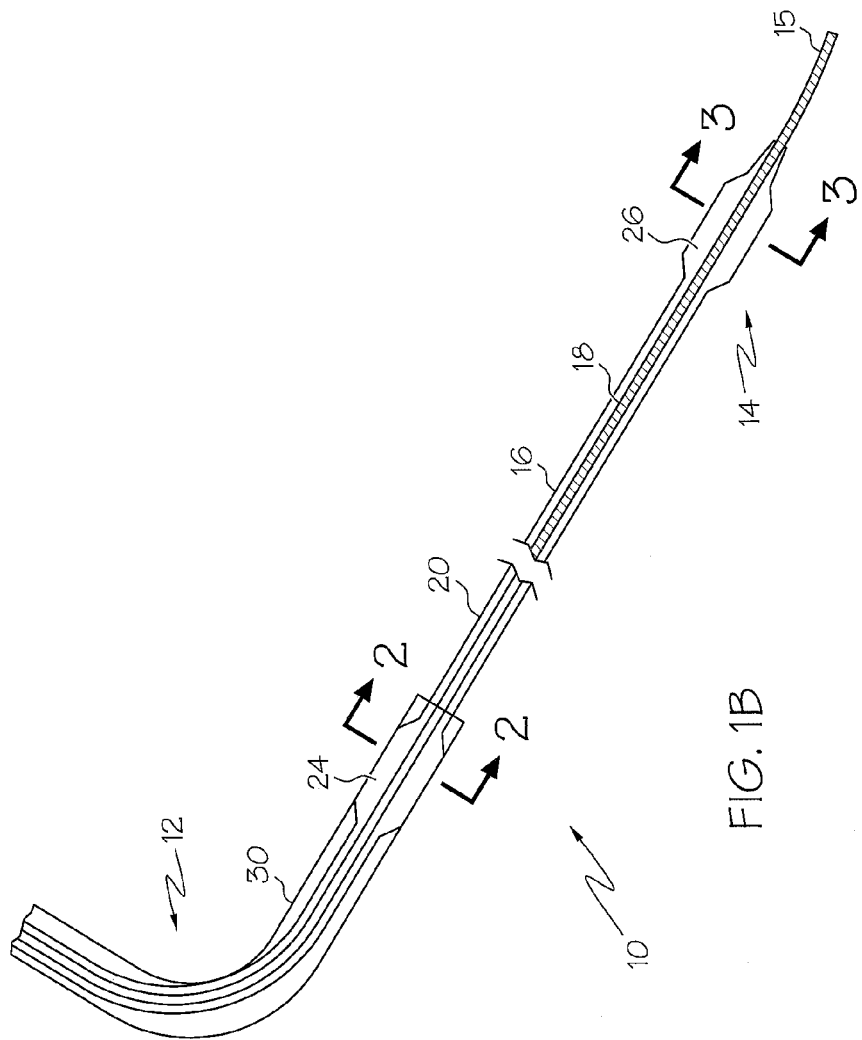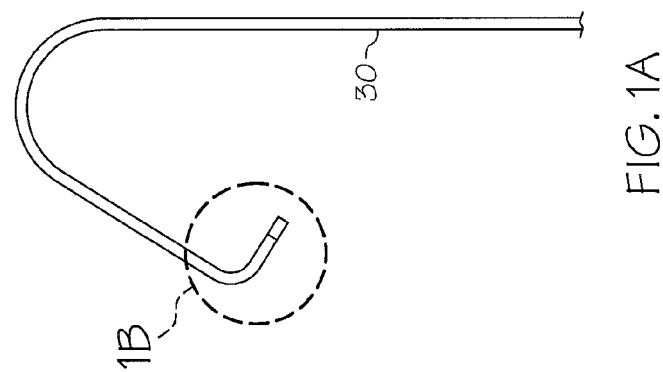

BALLOON CATHETER INCLUDING MULTIPLE CHAMBER BALLOON WITH VARYING RADIUS

CROSS-REFERENCE TO RELATED APPLICATIONS

This Application is a continuation of application Ser. No. 11/367,778, filed Mar. 3, 2006.

STATEMENT REGARDING FEDERALLY SPONSORED RESEARCH

Not Applicable

FIELD OF THE INVENTION

In some embodiments this invention relates to a catheter used to treat chronic total occlusions.

BACKGROUND OF THE INVENTION

Percutaneous transluminal coronary angioplasty (PTCA) and stenting are therapeutic medical procedures used to increase blood flow through the coronary arteries and can often be used as alternatives to coronary bypass surgery. In PTCA procedures, the angioplasty balloon is inflated within the stenosed vessel, at the location of an atheroma or plaque deposit, in order to shear and disrupt the wall components of the vessel to obtain an enlarged lumen. Stenting involves implanting an endoluminal prosthesis in the vessel to maintain patency following the procedure. In order to initiate these procedures, one must first introduce a guide wire into the lumen of the vessel to serve as a conduit for other interventional devices, such as angioplasty balloons and stent delivery systems. This guide wire must be advanced into a position past the location of the atheroma or plaque deposit.

In some cases, a vessel may be totally occluded, and even a guide wire cannot be introduced. This condition is referred to as a chronic total occlusion. In order to advance the guide wire across a calcified, tough and resistant lesion it is necessary to "deep seat" the guide catheter. Often when the physician is trying to get the wire across a tough lesion, the guide will back out of its position in the aortic arch by the force applied to the wire. Undesirably, these situations cause trauma that physicians would like to avoid. In addition, it has been recognized that proper positioning of the guide wire relative to the center of the occlusion is important because, depending upon the configuration of the occlusion, the tip of the guide wire has a natural tendency to be directed toward the side of the occlusion rather than the center. This can result in vessel perforation, dissection and inability to cross the occlusion.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a catheter assembly comprising a flexible elongated balloon catheter and a flexible guide catheter. The balloon catheter has a plurality of balloons. A first balloon is positioned at the distal end region of the balloon catheter. The first balloon has at least one chamber. The first balloon has an unexpanded state, an intermediate state and an expanded state. In use, when in an expanded state, the first balloon engages the vessel wall, thereby securing the balloon catheter to the vessel wall. An intermediate state is between an expanded state and an unexpanded state. If the first balloon has a plurality of chambers, at least one of the chambers will be in an intermediate state or an expanded state so that the first balloon engages the vessel wall and the tip of the catheter can be steered to the optimal position for getting the guide wire across the lesion. Hereinafter the first balloon will be referred to as a steering balloon. The steering balloon can be used to obtain the optimal position for the guide wire. In some embodiments of the invention, the steering balloon also has other characteristics such as securing the balloon catheter to the vessel wall or stabilizing the catheter assembly.

The balloon catheter has a second balloon positioned proximal to the steering balloon. In use, when inflated, the second balloon engages the guide catheter. This stabilizes the catheter assembly to help prevent the guide catheter from moving relative to the balloon catheter. Hereinafter the second balloon will be referred to as a stabilizing balloon. The stabilizing balloon can be used to prevent movement of the balloon catheter relative to the guide catheter. In some embodiments of the invention, the stabilizing balloon also has other characteristics such as securing the balloon catheter within the vessel.

Some embodiments have a third balloon positioned proximal to the steering balloon and distal to the stabilizing balloon. In use, when inflated, the third balloon engages the vessel wall. This helps to anchor the balloon catheter to the vessel wall while the at least one chamber of the steering balloon goes from an unexpanded state to either an intermediate state or an expanded state. Hereinafter, the third balloon will be referred to as an anchoring balloon. The anchoring balloon can be used to secure the balloon catheter to the vessel wall. In some embodiments of the invention, it also has other characteristics such as being useful to position the guide wire relative to the occlusion or to help prevent movement of the balloon catheter relative to the guide catheter.

In at least one embodiment, the invention is directed to a catheter assembly comprising a flexible elongated balloon catheter and a flexible elongated guide catheter. The interior surface of the guide catheter forms a lumen with a diameter large enough to allow it to slide over the balloon catheter when the balloons engaged to the balloon catheter are in an unexpanded state. The balloon catheter has a steering balloon with at least one chamber engaged to the balloon catheter at the distal end region and a stabilizing balloon engaged to the balloon catheter proximal to the steering balloon. In use, when the stabilizing balloon is in an expanded state it fixedly engages the interior surface of the guide catheter, preventing movement of the balloon catheter relative to the guide catheter. In use, when the at least one chamber of the steering balloon is in an expanded state it is engaged to the vessel wall, thereby securing the balloon catheter to the vessel wall.

In at least one embodiment, the catheter assembly further comprises an anchoring balloon engaged to the balloon catheter proximally to the steering balloon and distally from the stabilizing balloon. In use, when the anchoring balloon is in an expanded state it is engaged to the vessel wall, further securing the balloon catheter to the vessel wall.

In at least one embodiment, the steering balloon of the catheter assembly has a plurality of chambers. Each chamber of the steering balloon has an unexpanded state, an intermediate state and an expanded state. An intermediate state is between an expanded state and an unexpanded state. In use, when at least one of the plurality of chambers is in an intermediate state or in an expanded state, the steering balloon engages the vessel wall, thereby securing the balloon catheter to the vessel wall. In addition, this allows the tip of the catheter to be steered to the optimal position for getting the guide wire across the lesion.

In all the various embodiments, the catheter assembly may have a radiopaque marker or be detectable by imaging modalities.

A physician can use all of the various embodiments to treat a patient with an occlusion of a body lumen.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 1 is an overall view of one embodiment of the catheter assembly with the balloons in an expanded state.

Figure 4:
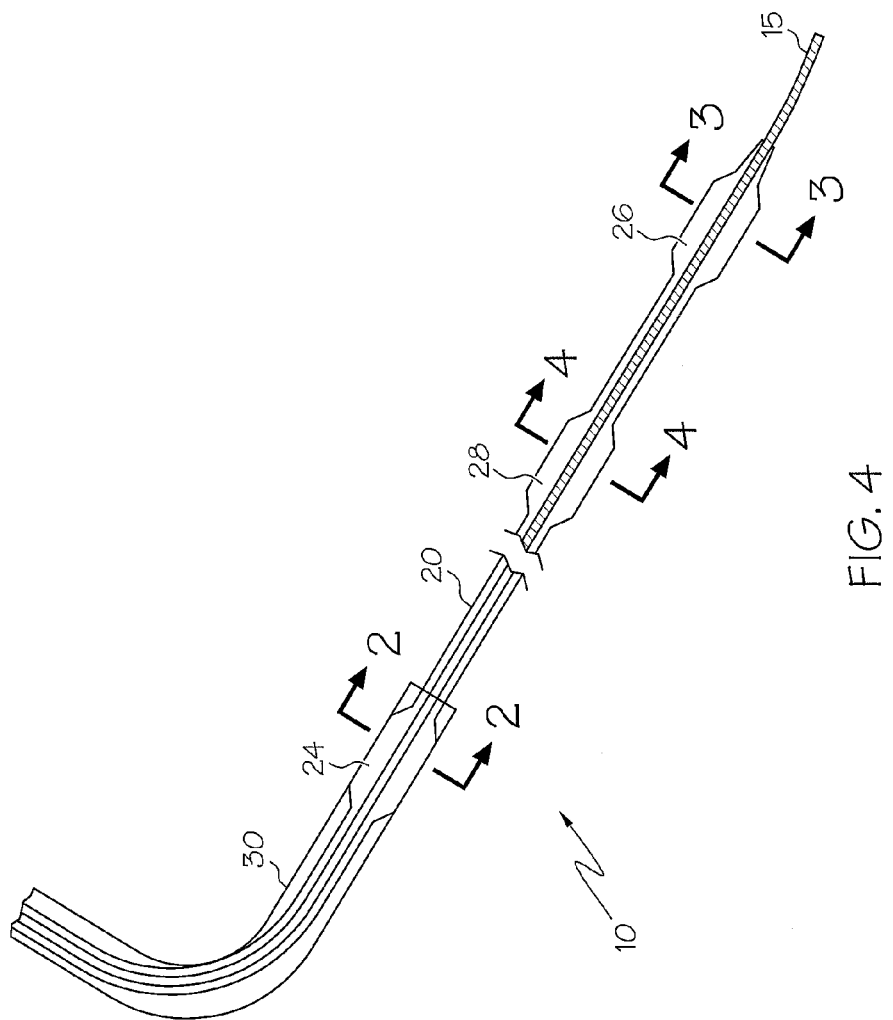
FIG. 4 is an overall view of another embodiment of the catheter assembly with a third balloon, an anchoring balloon, and all three balloons are in an expanded state.
Figure 5A:
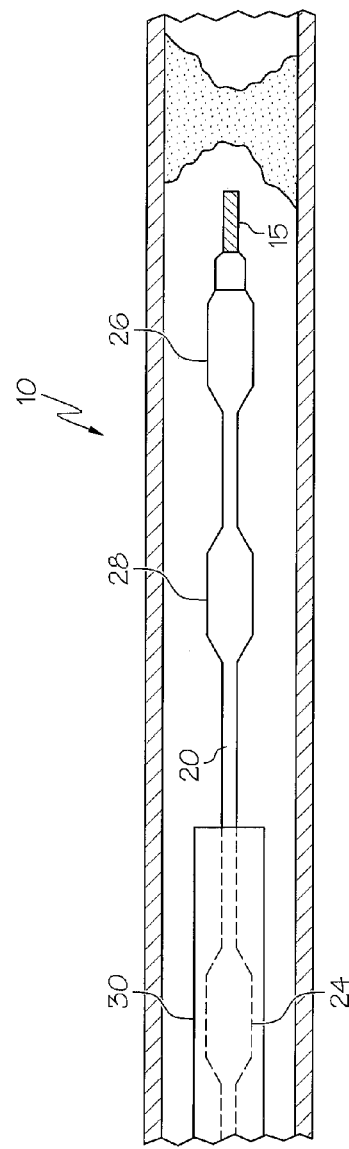
Figure 5B:
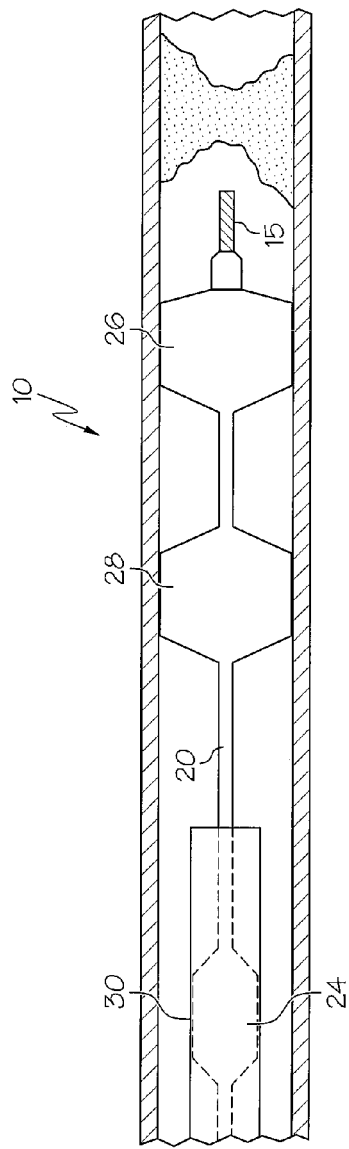
Figure 5C:
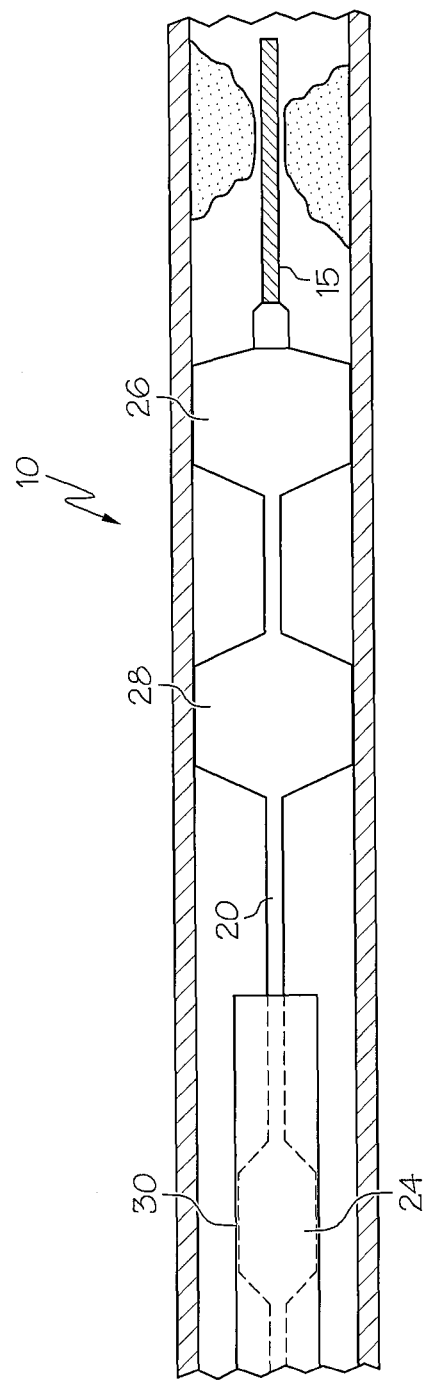

FIG. 5A-C illustrate the steps in an exemplary method performed using the embodiment of FIG. 4 in accordance with the principles of the present invention.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
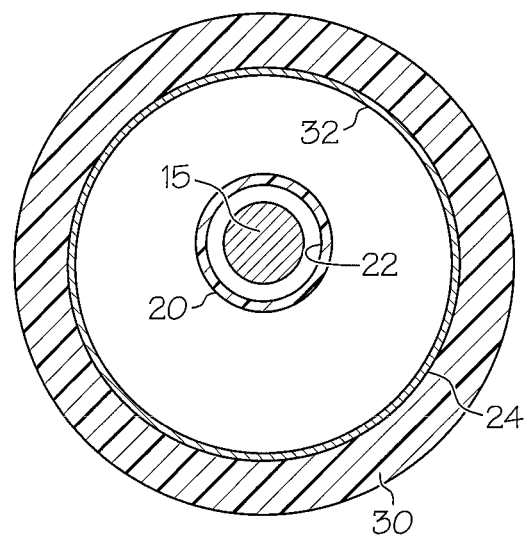
FIG. 2 is a cross sectional view of the catheter assembly of FIG. 1 along line 2-2 with the stabilizing balloon in an expanded state.

Referring now to the drawings which are for the purposes of illustrating embodiments of the invention only and not for purposes of limiting same, in at least one embodiment of the invention, an inventive catheter with at least two balloons is shown by way of example in FIG. 1 with additional details shown in the cross-sections of FIGS. 2-3.

In FIG. 1 the catheter assembly 10 comprises a guide catheter 30, a balloon catheter 20 with a stabilizing balloon 24 and a steering balloon 26, and an optional guide wire 15. The balloon catheter 20 typically has at least one shaft. In the embodiment shown, the shaft has a proximal end 12, a distal end 14, an exterior surface 16 and an interior surface 18. The body of the shaft is the area between the exterior surface 16 and the interior surface 18. The stabilizing balloon 24 is located proximal to the steering balloon 26.

In at least one embodiment, the stabilizing balloon 24 is made of compliant material, for example, but not limited to, nylon, and polyamines. In at least one embodiment, the stabilizing balloon 24 is made of semi-compliant material, for example, but not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. Other suitable balloon materials may also be used. The stabilizing balloon 24 can have a cross section that is cylindrical, oval, square or rectangular shape, or other similar shape.

In at least one embodiment, the steering balloon 26 is manufactured with semi-compliant material, for example, but not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. In at least one embodiment, the steering balloon 26 is manufactured with non-compliant material, for example, but not limited to, polyethylene terephthalates, polyacrylenesulfide, and copolyesters. In at least one embodiment, the steering balloon 26 is manufactured with compliant material, for example, but not limited to, nylon, and polyamines. Other balloon materials may also be used. The steering balloon 26 can have a cross section that is cylindrical, oval, square or rectangular shape, or other similar shape.

In order to inflate the steering balloon 26 and the stabilizing balloon 24, the balloon catheter 20 has at least one inflation lumen. In at least one embodiment, the at least one inflation lumen is within the shaft of the balloon catheter 20. In at least one embodiment, both the stabilizing balloon 24 and the steering balloon 26 have a common inflation lumen in fluid communication with each balloon. In at least one embodiment, the stabilizing balloon 24 and the steering balloon 26 have separate inflation lumens.

The invention is also directed to a catheter system comprising a first balloon and a second balloon, the first and second balloon coaxially disposed about a catheter shaft, the second balloon located proximal to the first balloon, one of the first and second balloon being compliant, the other being non-compliant, or semi-compliant. The first balloon is typically located about 1 centimeter to about 20 centimeters from the second balloon. Any other spacing is also within the scope of the invention.

The invention is also directed to a catheter system comprising first and second balloons, the first balloon located within a catheter, the second balloon located outside a catheter. The first balloon and second balloons may optionally be arranged in a co-linear relationship, disposed about the same catheter. The first balloon may be proximal to the second balloon. The first balloon is engaged to the catheter preventing relative movement in a longitudinal direction between the second balloon and the catheter.

FIG. 2 is a cross section of the catheter assembly shown in FIG. 1 taken along line 2-2. The guide catheter 30 has a shaft with an interior surface that defines a lumen 32. The lumen 32 has a diameter large enough to allow the balloon catheter 20 to slide through the lumen 32 of the guide catheter 30. The interior surface of the shaft of the balloon catheter defines a lumen 22. The elongated guide wire 15 extends within the lumen 22 of the balloon catheter 20. As shown in FIG. 2, the stabilizing balloon 24 is engaged to the guide catheter 30. The stabilizing balloon 24 has an unexpanded state and an expanded state. Typically, the radius of the stabilizing balloon 24 in an expanded state is less than the radius of the steering balloon 26 in an expanded state. In at least one embodiment, the radius of the stabilizing balloon 24 in an expanded state is slightly larger the radius of the lumen of the guide catheter 30 to ensure the stabilizing balloon 24 engages the guide catheter 30. Inflation of the stabilizing balloon 24 causes the stabilizing balloon 24 to fixedly engage the interior surface of the guide catheter 30 and prevent the balloon catheter 20 from moving relative to the guide catheter 30.

In at least one embodiment, the stabilizing balloon 24 is at least 0.068 inches in diameter in an expanded state. The exact diameter of the expanded stabilizing balloon 24 will depend on the size of the guide catheter 30 to which it is to be engaged. The diameter of the stabilizing balloon 24 may range from about 0.066" to about 0.070" (about 1.7 mm to about 1.8 mm) depending upon whether a 6F or 7F guide catheter is used.

Figure 3A:
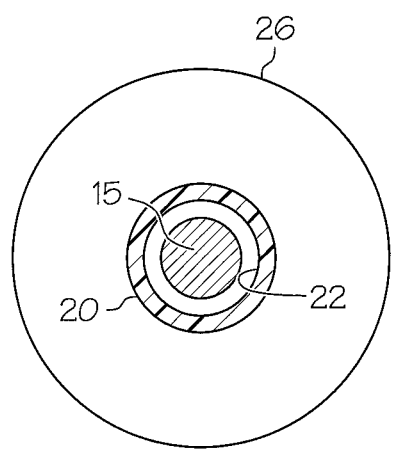
FIG. 3a is a cross sectional view of the catheter assembly of FIG. 1 along line 3-3 with the steering balloon in an expanded state.
Figure 3B:
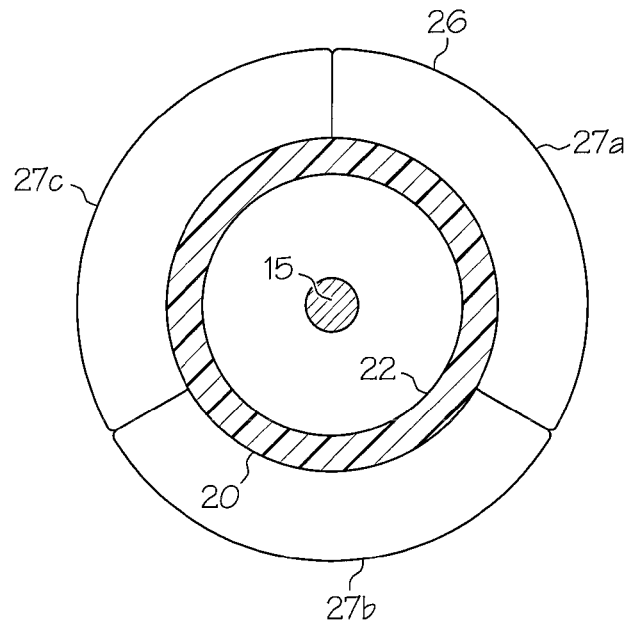
FIG. 3b is a cross sectional view of the catheter assembly with a three chamber steering balloon in an expanded state.

FIGS. 3a and 3b show a cross section of the catheter assembly 10 of FIG. 1, taken along line 3-3 with the steering balloon 26 in an expanded state. FIG. 3a shows an embodiment where the steering balloon has one chamber. It is also within the scope of the invention for the steering balloon to have two, three, four, five, six or more chambers. More generally, the steering balloon 26 may have a plurality of chambers. FIG. 3b, for example, shows an embodiment of the steering balloon 26 with three chambers 27a,b,c.

In the embodiment shown in FIG. 3a, the interior surface of the shaft of the balloon catheter defines a lumen 22. The elongated guide wire 15 extends within the lumen 22 of the balloon catheter 20. The steering balloon 26 is located at the distal end region of the balloon catheter 20. The steering balloon 26 has an unexpanded state and an expanded state. Desirably, the radius of the steering balloon 26 in an expanded state is greater than the radius of the steering balloon 26 in an unexpanded state. The steering balloon 26 is typically sized such that in an expanded state it engages the vessel wall, thus securing the balloon catheter 20 to the vessel wall.

In at least one embodiment, the diameter of the steering balloon 26 is at least 1.5 mm in an expanded state. The exact radius of the steering balloon 26 will depend upon the size of the lumen within which the steering balloon 26 will be expanded. Therefore, the steering balloon 26 can have any radius desired.

As discussed above, FIG. 3b shows a cross section of an embodiment of the catheter assembly with a multi-chamber 27 steering balloon 26 with three chambers 27a,b,c. Each chamber of the multi-chamber 27 steering balloon 26 has an unexpanded state, an intermediate state and an expanded state. Each chamber has a radius in an expanded state that is greater than the radius of each chamber in an intermediate state and the radius of each chamber in an intermediate state is greater than the radius of each chamber in an unexpanded state. Depending upon the topography of the vessel wall, the steering balloon 26 can engage the vessel wall when at least one of the chambers 27 of the plurality of chambers 27 is in an intermediate state. Thus, in order for the steering balloon 26 to secure the balloon catheter 20 to the vessel wall, at least one and, typically, each chamber 27a,b,c of the steering balloon 26 is either in an intermediate state or in an expanded state. In at least one embodiment, the steering balloon 26 is manufactured with semi-compliant material. In the embodiment of FIG. 3, the three chambers 27a,b,c of the steering balloon 26 are all in an expanded state. However, in at least one embodiment, at least one of the three chambers 27a,b,c is not in an expanded state.

Figure 3C:
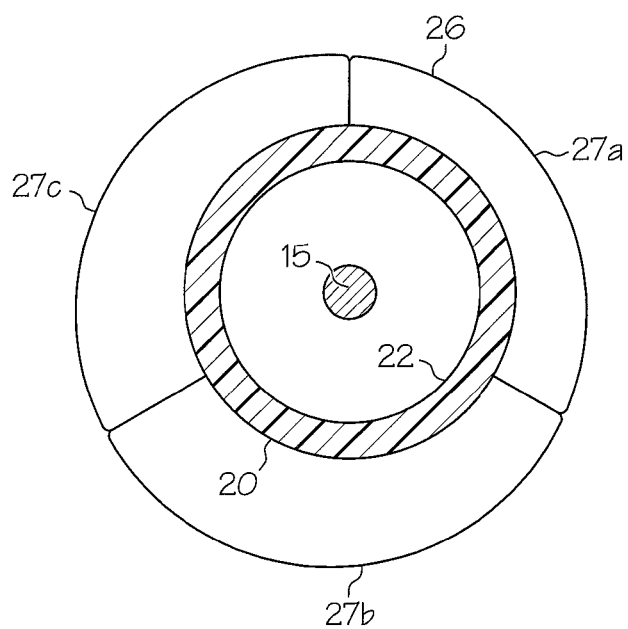
FIG. 3c is a cross sectional view of the catheter assembly with one chamber of the three chamber steering balloon inflated with a lower pressure than the other chambers.

For example, FIG. 3c shows an embodiment of the multi-chamber steering balloon 26 with one chamber 27a in an intermediate state while the other chambers 27b,c are in an expanded state. A steering balloon 26 with a plurality of chambers 27 permits the physician to inflate one or more and, typically, all of the chambers 27 to an intermediate or expanded state. The multi-chamber steering balloon 26 as depicted in FIG. 3c shows only one chamber 27a in an intermediate state. In addition, as shown in FIG. 3c, the radius of a particular chamber 27b or c may not be constant. The radius of chamber 27c where chamber 27c engages chamber 27b is larger than the radius of chamber 27c where chamber 27c engages chamber 27a. This allows optimal positioning of the catheter assembly within the diameter of the body lumen in relation to the occlusion so that the guide wire 15 can be pushed through the occlusion. In at least one embodiment, each chamber 27 may be inflated with a different contrasting agent, detectable by imaging modalities such as X-Ray, MRI, ultrasound, etc., to allow precise positioning of the catheter by the physician.

In order to inflate the steering balloon 26 and the stabilizing balloon 24, the balloon catheter 20 has at least one inflation lumen in fluid communication with the steering balloon 26 and the stabilizing balloon 24. In at least one embodiment, the stabilizing balloon 24 and each chamber 27 of the steering balloon 26, have a separate and distinct inflation lumen in fluid communication therewith. In at least one embodiment, the stabilizing balloon 24 and one or more, and typically each, chamber 27 of the steering balloon 26 has a common inflation lumen in fluid communication therewith. In at least one embodiment, the at least one inflation lumen is located within the shaft of the balloon catheter 20.

FIG. 4 shows another embodiment of the catheter assembly 10. The catheter assembly 10 comprises a guide catheter 30, a balloon catheter 20 and, optionally, a guide wire 15. The balloon catheter 20 comprises an outer shaft and an inner shaft. The balloon catheter 20 further comprises a steering balloon 26, an anchoring balloon 28 and a stabilizing balloon 24. In FIG. 4, the steering balloon 26, the stabilizing balloon 24 and the anchoring balloon 28 are in an expanded state.

The stabilizing balloon 24 is proximal to the anchoring balloon 28. A cross section of this embodiment of the catheter assembly taken at the site of the stabilizing balloon 24, FIG. 4 along line 2-2, would have the same arrangement as the cross section of the stabilizing balloon 24 shown in FIG. 2. The inner shaft of the balloon catheter 20 has an interior surface defining a lumen 22. The elongated guide wire 15 extends within the lumen 22 of the balloon catheter 20. The guide catheter 30 has an interior surface that defines a lumen 32 with a diameter large enough to allow the balloon catheter 20 to slide through the lumen of the guide catheter 30. The stabilizing balloon 24 has an unexpanded state and an expanded state. The radius of the stabilizing balloon 24 in an expanded state is typically less than the radius of either the steering balloon 26 or the anchoring balloon 28 in an expanded state although in some embodiments, for example, in an embodiment in which the inventive device is designed for a tapered vessel, the radius of the expanded stabilizing balloon 24 may exceed that of the expanded steering balloon 26 and/or anchoring balloon 28. The radius of the stabilizing balloon 24 in an expanded state is larger than in an unexpanded state. In an expanded state the stabilizing balloon 24 is fixedly engaged to the guide catheter 30. In at least one embodiment, the stabilizing balloon 24 is at least 0.068 inches in diameter in an expanded state. The exact diameter of the expanded stabilizing balloon 24 will depend on the diameter of the guide catheter 30 to which it is to be engaged.

In at least one embodiment, the stabilizing balloon 24 is made of compliant material, for example, but not limited to, nylon, and polyamines In at least one embodiment, the stabilizing balloon 24 is made of semi-compliant material, for example, but not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. Other suitable balloon materials may also be used. The stabilizing balloon 24 can have a cross section that is cylindrical, oval, square or rectangular shape, or other similar shape.

The steering balloon 26 is engaged to the distal end region of the balloon catheter 20. A cross section of this embodiment of the catheter assembly 10 taken at the site of the steering balloon 26, FIG. 4 at line 3-3, would have the same arrangement as the cross section of the embodiment of the steering balloon 26 shown in FIG. 3a since the steering balloon 26 in this embodiment has one chamber. In at least one embodiment the steering balloon 26 has a plurality of chambers. In at least one embodiment, the steering balloon 26 has three chambers. A cross section of the catheter assembly 10 taken at the site of the steering balloon 26 in a multi-chamber 27 steering balloon embodiment would have the same arrangement as the cross-section of the embodiments of the multi-chamber 27 steering balloon 26 shown in FIG. 3b-c. The steering balloon 26 has an unexpanded state and an expanded state. The radius of the steering balloon 26 in an expanded state is greater than the radius of the steering balloon 26 in an unexpanded state. Inflation of the steering balloon 26 to an expanded state engages the steering balloon 26 to the vessel wall, thus securing the balloon catheter 20 to the vessel wall.

In at least one embodiment, the steering balloon 26 has a diameter of at least 1.5 mm in an expanded state. The exact diameter of the steering balloon 26 will depend upon the size of the lumen within which the steering balloon 26 will be expanded. Therefore, the steering balloon 26 can have any diameter desired.

In at least one embodiment, the steering balloon 26 is manufactured with semi-compliant material, for example, but not limited to, ethylene-vinyl acetate, polyvinyl chloride (PVC), olefin copolymers or homopolymers, polyethylenes, polyurethanes, cross-linked low density polyethylenes (PETs), highly irradiated linear low density polyethylene (LDPE), acrylonitrile polymers and copolymers, acrylonitrile blends and ionomer resins. In at least one embodiment, the steering balloon 26 is manufactured with non-compliant material, for example, but not limited to, polyethylene terephthalates, polyacrylenesulfide, and copolyesters. In at least one embodiment, the steering balloon 26 is manufactured with compliant material, for example, but not limited to, nylon, and polyamines. Other suitable balloon materials may also be used. The steering balloon 26 can have a cross section that is cylindrical, oval, square or rectangular shape, or other similar shape.

The anchoring balloon 28 is proximal to the steering balloon 26 and distal to the stabilizing balloon 24. The anchoring balloon 28 typically has one chamber. A cross section of this embodiment of the catheter assembly taken at the site of the anchoring balloon 28, FIG. 4 along line 4-4, would have the same arrangement as the cross section of the steering balloon 26 embodiment shown in FIG. 3a. The anchoring balloon 28 has an unexpanded state and an expanded state. In at least one embodiment, the radius of the anchoring balloon 28 in an expanded state is substantially similar to the radius of the steering balloon 26 in an expanded state. In at least one embodiment, the radius of the anchoring balloon 28 in an expanded state is different than the radius of the steering balloon 26 in an expanded state due to the tapering of the vasculature. In an expanded state the anchoring balloon 28 engages the vessel wall, thus further securing the balloon catheter 20 while the steering balloon 26 is positioned.

In at least one embodiment, the anchoring balloon 28 has a diameter of at least 1.5 mm in an expanded state. The exact diameter of the expanded anchoring balloon will depend on the size of the vessel to which it is to be anchored. The exact diameter of the anchoring balloon 28 will depend upon the size of the lumen within which the anchoring balloon 28 will be expanded. Therefore, the anchoring balloon 28 can have any diameter desired.

In at least one embodiment, the anchoring balloon 28 is manufactured with semi-compliant material, for example, but not limited to, ethylene-vinyl acetate, polyvinyl chloride (PVC), olefin copolymers or homopolymers, polyethylenes, polyurethanes, crosslinked low density polyethylenes (PETs), highly irradiated linear low density polyethylene (LDPE), acrylonitrile polymers and copolymers, acrylonitrile blends and ionomer resins. In at least one embodiment, the anchoring balloon 28 is manufactured with compliant material, for example, but not limited to, nylon, and polyamines. Other suitable balloon materials may also be used. The anchoring balloon 28 can have a cross section that is cylindrical, oval, square or rectangular shape, or other similar shape.

In order to inflate the steering balloon 26, the anchoring balloon 28 and the stabilizing balloon 24, the balloon catheter 20 has at least one inflation lumen in fluid communication with the steering balloon 26, the anchoring balloon 28 and the stabilizing balloon 24. In at least one embodiment, the stabilizing balloon 24, the anchoring balloon 28 and the steering balloon 26 each have a separate and distinct inflation lumen in fluid communication therewith. In at least one embodiment, the stabilizing balloon 24, the anchoring balloon 28 and the steering balloon 26 have a common inflation lumen in fluid communication with the balloons. In at least one embodiment, the at least one chamber of the steering balloon is inflated with at least one contrasting agent, detectable by imaging modalities such as X-Ray, MRI, ultrasound, etc., to allow precise positioning of the catheter by the physician. If a plurality of contrasting agents are used, then one contrasting agent is used to inflate one chamber, a second contrasting agent is used to inflate a second chamber, etc.

The invention is also directed to a catheter system comprising a first balloon, a second balloon and a third balloon, the first, second and third balloons coaxially disposed about a catheter shaft, the third balloon located proximal to the first balloon and distal to the second balloon. The third balloon may be located about 1 cm to about 5 cm from the first balloon and about 5 cm to about 14 cm from the second balloon. In some embodiments, the third balloon may be located less than 1 cm from the first balloon or more than 5 cm from the first balloon. In some embodiments, the third balloon may be located less than 5 cm or more than 14 cm from the second balloon. Other separations between the balloons are also contemplated.

The invention is also directed to a catheter system comprising first, second and third balloons, the first balloon located within a catheter, the second and third balloons located outside a catheter. The first balloon, second balloon and third balloon are co-linearly arranged along the catheter system. The first balloon is proximal to the third balloon and the third balloon is proximal to the second balloon. The first balloon is engaged to the catheter.

FIG. 5A-C illustrates how a physician treating a patient with an occlusion can use one of the above embodiments of the present inventive catheter, in particular the embodiment illustrated in FIG. 4. First, the physician threads the guide wire through the patient's vasculature until the site of the occlusion is reached. Then, as shown in FIG. 5a, the physician threads the catheter assembly over the guide wire. Areas of the catheter assembly that are detectable by imaging modalities can be used to visualize the location of the catheter assembly 10 relative to the occlusion. At the site of the occlusion, the physician will inflate the stabilizing balloon 24 so that the balloon catheter 20 is fixedly engaged to the guide catheter 30.

Next, as shown in FIG. 5b, the physician can inflate the anchoring balloon 28, if the catheter assembly has an anchoring balloon 28. Inflation of the anchoring balloon 28 will engage the catheter assembly to the vessel wall. Then the physician can inflate the at least one chamber of the steering balloon 26 to an intermediate state or an expanded state so that the steering balloon is engaged to the vessel wall. Note it is within the scope of the invention for the anchoring balloon to be inflated before the steering balloon, for the steering balloon to be inflated prior to the anchoring balloon or the steering and anchoring balloons to be inflated simultaneously. Typically, the steering balloon and the anchoring balloon will be inflated before the physician begins to advance the guide wire 15 through the occlusion.

In at least one embodiment, in order to visualize the placement of the distal end of the catheter assembly 10 and the guide wire 15 relative to the center of the occlusion, the physician can use a contrasting agent to inflate the chamber or chambers of the steering balloon 26 to either an intermediate state or an expanded state. In at least one embodiment, the catheter assembly 10 can be positioned relative to the center of the occlusion by visualizing the radiopaque markers on the catheter assembly 10.

Once the catheter assembly 10 is in the desired position the physician can optionally advance the guide wire 15 through the occlusion. Once the guide wire 15 has traversed through the occlusion, the physician can proceed with the desired treatment, if any, e.g. advancing a treatment catheter to the site of the occlusion, the treatment catheter may carry a stent or other implantable device.

In some embodiments the catheter assembly, or a portion of the assembly may include one or more areas, bands, coatings, members, etc. that is (are) detectable by imaging modalities such as X-Ray, MRI, ultrasound, etc. In some embodiments at least a portion of the steering balloon 26 and/or adjacent assembly is at least partially radiopaque.

It is also within the scope of the invention for the catheter systems disclosed herein to be used for stent delivery. In the case of a balloon expandable stent, typically, the distal most balloon of the device would carry the stent. In the case of a self-expanding stent, the catheter system may be outfitted with a pull-back sheath, as is known in the art, to restrain the self-expanding stent until it is delivered to a desired bodily location.

The invention is also directed to methods of using any of the inventive devices disclosed above.

In one embodiment, the invention is directed to a method of treating an occlusion in a body lumen comprising the steps of advancing a catheter system having at least two balloons and a catheter to the site of an occlusion, inflating a first balloon to engage an interior surface of the catheter, and inflating a second balloon to engage a surface of a body lumen. Any of the inventive catheter systems disclosed above may be used.

The invention is also directed to a method of treating a body lumen comprising the steps of providing a catheter with an expandable region, the expandable region comprising a plurality of compartments, none of which extend all of the way around the circumference of the stent, selectively inflating one or more of the chambers to a pressure which differs from the pressure of the remaining chambers. Optionally, each of the compartments may be in the form of a separate balloon. In some embodiments, all of the chambers may form one balloon, supplied by a single inflation lumen.

The invention is also directed to a catheter with a plurality of balloons arranged circumferentially side by side about the catheter. Each balloon of the plurality of balloons extends lengthwise along the catheter. Each balloon has an unexpanded state, an intermediate state and an expanded state. When the plurality of balloons are inflated to either an intermediate state or an expanded state, the balloons may optionally engage the walls of the vasculature, or other surrounding surface. The plurality of balloons may be inflated simultaneously or separately. In at least one embodiment, each balloon of the plurality of balloons has a separate inflation lumen. In at least one embodiment, the plurality of balloons have a common inflation lumen.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A catheter system, the catheter system comprising:
a balloon catheter, the balloon catheter comprising:
a shaft, the shaft defining a first inflation lumen;
a first balloon engaged to the shaft at a first longitudinal position, the first balloon having a circumference, the first balloon having a plurality of chambers, each chamber having a wall, the wall comprising a first wall section extending radially, a second wall section extending radially, and a third wall section extending circumferentially and connecting the first and second wall sections, the circumference of the first balloon formed only by the third wall sections of the plurality of chambers, each of the plurality of chambers being in fluid communication with the first inflation lumen, the plurality of chambers comprising a first chamber, wherein the first and second wall sections of the first chamber extend for different distances from the shaft when the first chamber contains inflation fluid.

2. The catheter system of claim 1, wherein the first balloon is in either an intermediate state or an expanded state when it contains inflation fluid in at least one of the plurality of chambers.

3. The catheter system of claim 1, the balloon catheter further comprising a second balloon, the second balloon engaged to the shaft at a second longitudinal position, the second longitudinal position being proximal to the first longitudinal position.

4. The catheter system of claim 3, the second balloon in fluid communication with the first inflation lumen.

5. The catheter system of claim 3, the shaft further defining a second inflation lumen, the second balloon in fluid communication with the second inflation lumen.

6. The catheter system of claim 3, further comprising a guide catheter, the guide catheter defining a lumen, the lumen of the guide catheter having a diameter sufficient for the balloon catheter to be disposed within.

7. The catheter system of claim 6, the second balloon being engaged to an inner surface of the guide catheter when the second balloon is in an expanded state.

8. The catheter system of claim 3, the balloon catheter further comprising a third balloon, the third balloon being engaged to the shaft at a third longitudinal position, the third longitudinal position being between the first and second longitudinal positions.

9. The catheter system of claim 1, the third wall sections of the plurality of chambers forming a continuous outer surface of the first balloon.

10. The catheter system of claim 8, the second balloon having a single chamber and the third balloon having a single chamber.

* * * * *